United States Patent
Faherty et al.

(10) Patent No.: US 9,642,640 B2
(45) Date of Patent: May 9, 2017

(54) LITHOTRIPTER WITH IMPROVED STERILIZATION TIME

(71) Applicant: Gyrus ACMI, Inc., Southborough, MA (US)

(72) Inventors: Richard C. Faherty, Watertown, MA (US); Lawrence J. St. George, Sudbury, MA (US)

(73) Assignee: Gyrus ACMI, INC., Southborough, MA (US)

( * ) Notice: Subject to any disclaimer, the term of this patent is extended or adjusted under 35 U.S.C. 154(b) by 187 days.

(21) Appl. No.: 14/450,363

(22) Filed: Aug. 4, 2014

(65) Prior Publication Data

US 2016/0030069 A1    Feb. 4, 2016

(51) Int. Cl.
*A61B 17/22*   (2006.01)
*A61B 17/225*  (2006.01)
*A61B 17/00*   (2006.01)
*A61B 90/00*   (2016.01)

(52) U.S. Cl.
CPC ...... *A61B 17/225* (2013.01); *A61B 17/22004* (2013.01); *A61B 17/22012* (2013.01); *A61B 2017/0046* (2013.01); *A61B 2017/00469* (2013.01); *A61B 2017/00477* (2013.01); *A61B 2017/22014* (2013.01); *A61B 2017/22027* (2013.01); *A61B 2017/22079* (2013.01); *A61B 2090/0813* (2016.02); *A61B 2217/005* (2013.01); *A61B 2217/007* (2013.01)

(58) Field of Classification Search
CPC ...... A61B 17/22012; A61B 17/320068; A61B 2017/22014; A61B 2017/22079; A61B 2017/32008; A61B 2217/005; A61B 17/22004; A61B 17/225; A61B 17/32002; A61B 2017/320028; A61B 2017/320064; A61B 17/03
USPC ............................ 606/128, 169, 171; 604/22
See application file for complete search history.

(56) References Cited

U.S. PATENT DOCUMENTS

| | | | |
|---|---|---|---|
| 4,660,573 A | | 4/1987 | Brumbach |
| 4,989,588 A | | 2/1991 | Kubota et al. |
| 5,335,661 A | | 8/1994 | Koblanski et al. |
| 5,427,118 A | | 6/1995 | Nita et al. |
| 5,669,923 A | * | 9/1997 | Gordon .............. A61B 10/0266 604/22 |
| 5,722,980 A | * | 3/1998 | Schulz ............. A61B 17/22012 604/22 |

(Continued)

*Primary Examiner* — Katherine M Shi
(74) *Attorney, Agent, or Firm* — Vivacqua Law, PLLC; Gerald P. Kazanjian

(57) ABSTRACT

An apparatus and method are presented for a lithotripter comprising a handle, a driver resource contained within the handle, a probe housed within the handle, an extension which may be the probe, a shielding insert, or a removable passageway which extends through a central lumen of the driver resource and protects the central lumen from surgical debris when in use and as a result reduces time required to perform sterilization. Sealing means may be provided to connect the probe into the handle, including a ferrule, collet, split collet, screw connection, O-rings, or a combination thereof to further limit debris entering the central lumen of the handle. It is contemplated that the device of the present invention is capable of achieving a four minute flash cycle validation.

4 Claims, 3 Drawing Sheets

(56) References Cited

U.S. PATENT DOCUMENTS

| | | | |
|---|---|---|---|
| 5,741,272 A * | 4/1998 | Kuhne | A61B 17/22012 604/22 |
| 5,843,109 A * | 12/1998 | Mehta | B06B 1/0618 604/22 |
| 6,149,656 A * | 11/2000 | Walz | A61B 17/22012 606/127 |
| 6,558,397 B2 | 5/2003 | Hirt et al. | |
| 6,875,220 B2 | 4/2005 | Du et al. | |
| 8,038,630 B2 | 10/2011 | Pal et al. | |
| 2002/0010477 A1* | 1/2002 | Hirt | A61B 17/22012 606/128 |
| 2002/0010486 A1* | 1/2002 | Hirt | A61B 17/22012 606/169 |
| 2010/0087789 A1* | 4/2010 | Leeflang | A61B 17/3207 604/265 |
| 2012/0053577 A1 | 3/2012 | Lee et al. | |
| 2013/0253387 A1 | 9/2013 | Bonutti et al. | |
| 2014/0121458 A1 | 5/2014 | St. George | |

\* cited by examiner

US 9,642,640 B2

LITHOTRIPTER WITH IMPROVED STERILIZATION TIME

FIELD OF THE INVENTION

The present invention relates to an improved lithotripter, more particularly to an apparatus and method for protecting an internal lumen of a lithotripter handle from surgical waste and to provide for faster sterilization procedures.

BACKGROUND

Over the past several decades, several advances have been made in the field of endoscopy, and in particular relating to the breaking up of physiologic calculi in the bile ducts, urinary tract, kidneys, and gall bladder. Physiological calculi in these regions may block ducts and cause a patient a substantial amount of pain and therefore must be broken down and/or removed. Different techniques have been developed to break up stones, including ultrasonic lithotripsy, pneumatic lithotripsy, electro-hydraulic lithotripsy (EHL), and dissolution of calculi using YAG or holmium lasers, for example.

A number of rigid solid or tubular probe-based lithotripsy devices that use ultrasonic or pneumatic energy to break the stone into smaller pieces for easier removal from the patient's urologic system have been developed. For example, the Olympus LUS-2, the Gyrus ACMI Cyberwand, and the Swiss Lithoclast are such devices. They may function by having ultrasonic or acoustic frequency energy transmitted down a stiff metal probe and delivered by contact to a kidney stone. Ultrasonic lithotripters generally require tuned probes and the effectiveness of these lithotripters depend on their ability to maintain resonance down the length of the probe (i.e. ultrasonic energy does not travel well around bends or turns). It is believed that probe bending can dissipate enough heat to seriously damage adjacent tissue or the endoscopic device itself, in addition to the loss of energy transfer to the tip of the probe.

For procedures performed with a tubular probe device, suction of liquid and debris during the lithotripsy procedure may be possible via the center of the tubular probe. Some devices may incorporate and deliver a lower frequency energy component to the kidney stone either through the same probe or via a second probe; this second probe is usually coaxial to the ultrasonic energy probe (i.e. the Cyberwand). This secondary, lower frequency energy shows evidence of improving the stone breaking efficiency over a solely ultrasonic energy approach.

Throughout the procedure, bodily waste including blood, stone debris, fluids and/or tissue have been removed from the patient through active suction and have passed through the lithotripsy probe and a central lumen of the handpiece. Most lithotripters include interchangeable probes that are added and removed from the lithotripter depending on the particular need for a particular procedure. The probe may be removed from sterile packaging, removed from non-sterile packaging and subsequently sterilized, or sterilized and reused from a previous procedure, and connected to the handpiece after the surgical handpiece has been sterilized. After a procedure is performed, the one or more probes are typically removed from connection at a distal end of a handpiece and may be discarded or sterilized for reuse in a subsequent procedure. The handpiece, including the internal lumen which may still contain bodily waste is subsequently processed for sterilization. Sterilization procedures that might occur on a lithotripsy device include wet/steam sterilization, dry heat sterilization, ethylene oxide, or sporicidal chemicals, for example.

In the case of an ultrasonic lithotripsy device, the evacuation path of the waste liquid is commonly through the center of the driver. If the ultrasonic driver is massive enough and the lumen is small enough, and the preferred sterilization method is autoclaving, it may be difficult to achieve a high enough temperature in the center of the ultrasonic driver to sufficiently sterilize the full length of the central lumen.

A potential result of bodily waste remaining in the central lumen of the handpiece or perhaps being rinsed out quickly before entering the sterilizer is that complete sterilization of the device with a four minute flash cycle, for example, may not be possible. However, in certain situations when fast sterilization is needed, this type of sterilization procedure may be run without fully sterilizing the device.

It is contemplated that there is a need for a lithotripter that allows for reliably eliminating a bulk of bodily waste to facilitate rapid sterilization cycles. This can result in practitioner and patient confidence that a complete sterilization has been achieved before reusing the device on a subsequent procedure.

SUMMARY OF THE INVENTION

The present invention meets one or more of the above needs by providing a protective removable passageway. The protective removable passageway may be the probe itself extended to the proximal end of the lithotripsy handle, a shielding insert surrounding at least a portion of the probe and contained from a proximal end to a distal end of the central lumen of the handpiece or a portion thereof, or an additional removable passageway extending along a portion of the central lumen of the handpiece.

Accordingly, pursuant to one aspect of the present invention, there is contemplated an apparatus, comprising a lithotripter, comprising a handle, the handle having a handle distal end and a handle proximal end; a driver resource contained within the handle; and a probe housed within the handle, the probe having a probe distal end and a probe proximal end, the probe distal end terminating at the distal end of the apparatus at a point distal from the handle distal end, the probe proximal end terminating proximal to the proximal end of the driver resource; wherein the probe proximal end is contained within the handle; wherein the driver resource causes the probe to move in a direction parallel with a longitudinal axis of the probe.

The invention may be further characterized by one or any combination of the features described herein, such as the probe further comprises one or more distal end seals, one or more proximal end seals, or a combination thereof; the one or more distal end seals, the one or more proximal end seals, or both are o-rings; a removable passageway extending through the handle and at least partially containing the probe, the removable passageway having a removable passageway proximal end and a removable passageway distal end; a shielding insert surrounding at least a portion of the probe and contained within the removable passageway within the handle, the shielding insert having a shielding insert proximal end and a shielding insert distal end; the shielding insert proximal end, the removable passageway proximal end, or both terminate proximal to the proximal end of the driver resource; the shielding insert further comprises one or more distal end seals, one or more proximal end seals, or a combination thereof; the one or more distal end seals, the one or more proximal end seals, or both are o-rings; one or more of the probe, the shielding insert, or the removable passageway may be further provided with a plug prior to removal of the probe, the shielding insert, or the removable passageway from a central passageway of the handle at either a distal end or a proximal end; a heat exchanger attachable to one or more of a distal handle end and a proximal handle end prior to performing a sterilization procedure; such sterilization procedure to support a viable four minute flash cycle where the device is validated to be sterile at the completion of the cycle.

Pursuant to another aspect of the present invention, there is contemplated an apparatus, comprising a lithotripter, comprising a handle, the handle having a handle distal end and a handle proximal end; a driver resource contained within the handle; a probe housed within the handle, the probe having a probe distal end and a probe proximal end, the probe distal end terminating at the distal end of the apparatus at a point distal from the handle distal end, the probe proximal end terminating distal to the distal end of the driver resource; and a shielding insert surrounding at least a portion of the probe within the handle, the shielding insert having a shielding insert proximal end and a shielding insert distal end, the shielding insert proximal end terminating proximal to the proximal end of the driver resource; wherein the driver resource causes the probe to move in a direction parallel with a longitudinal axis of the probe.

The invention may be further characterized by one or any combination of the features described herein, such as a removable passageway contained within a central lumen of the driver resource; the removable passageway is contained within a central lumen of the driver resource; one or more of the probe, the shielding insert, or the removable passageway may be further provided with a plug prior to removal of the probe, the shielding insert, or the removable passageway from a central passageway of the handle at either a distal end or a proximal end; a heat exchanger attachable to one or more of a distal handle end and a proximal handle end prior to performing a sterilization procedure; such sterilization procedure to support a viable four minute flash cycle where the device is validated to be sterile upon completion of the cycle.

Pursuant to yet another aspect of the present invention, there is contemplated a method, comprising attaching one or more heat exchangers to one or more of a distal handle end and a proximal handle end of a lithotripter, the lithotripter comprising a handle, the handle having a handle distal end and a handle proximal end; a probe housed within the handle, the probe having a probe distal end and a probe proximal end; a passageway extending through the handle at least partially containing the probe; and a shielding insert contained within the passageway, wherein the probe, the passageway, and the shielding insert are contained within a central lumen of a driver resource; and performing a sterilization procedure on the surgical device; wherein the one or more heat exchangers collect and transfer heat at least through a full length of the handle, particularly to the lumen contained within the handle.

Pursuant to yet another aspect of the present invention, there is contemplated a method, comprising the heat exchanger further comprising a coil, a bellows, a series of wings, or a combination thereof to encourage steam flow through the heat exchanger during sterilization to support a four minute flash cycle validation may be completed.

Further aspects, advantages and applicability will become apparent from the description provided herein. It should be understood that the description and specific examples are intended for purposes of illustration only and are not intended to limit the scope of the present disclosure.

DESCRIPTION OF THE DRAWINGS

The drawings described herein are for illustration purposes only and are not intended to limit the scope of the present disclosure in any way.

DETAILED DESCRIPTION OF THE INVENTION

Figure 1:
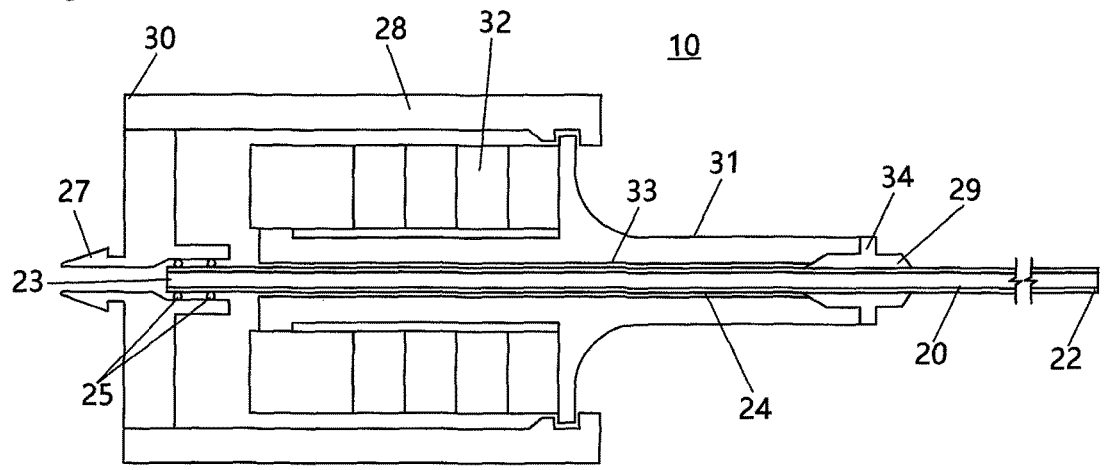
FIG. 1 is a cross-sectional view of one embodiment of a lithotripter in accordance with the teachings of the present invention.

The following description is merely exemplary in nature and is not intended to limit the present disclosure, application, or uses. Those skilled in the art may adapt and apply the teachings in its numerous forms, as may be best suited to the requirements of a particular use. The disclosures of all articles and references, including patent applications and publications, are incorporated by reference for all purposes. Other combinations are also possible as will be gleaned from the following claims, which are also hereby incorporated by reference into this written description.

As will be seen, the devices and methods taught herein offer an improved surgical instrument, preferably the surgical instrument is a lithotripter, which is capable of achieving complete sterilization in less time than those taught in the prior art. Examples of surgical procedures that the lithotripter of the teachings herein may be used to perform include lithotripsy to cause destruction of kidney stones. The lithotripter as discussed herein includes an interchangeable probe, a handpiece, and a driver resource. In one aspect, the present invention describes a lithotripter in which a probe, shielding insert, or removable passageway may extend from a distal end to a proximal end of a handpiece and which may be provided with one or more seals between the probe, shielding insert, or removable passageway and the handpiece at connection points at a distal end, at a proximal end, or both of a handpiece to prevent liquids or surgical debris from coming into direct contact with the inner surface of the handpiece. The teachings of the present invention may therefore be able to limit, minimize, or eliminate surgical waste products from coming into direct contact with the inner lumen of the lithotripter handle.

One embodiment of the invention may use a shielding insert as a protective removable passageway extending through the handle of the lithotripter assembly. The shielding insert may house a portion of the lithotripter probe or the lithotripter probe may extend through the entire length of the shielding insert. The shielding insert may be removably secured to the inner passageway of the lithotripter handpiece. Suction at the proximal end of the handpiece may make direct contact with the shielding insert, the lithotripsy probe, or both.

The probe may be any probe that is suitable to perform a lithotripsy procedure. The probe may be rigid, semi-rigid, flexible, include a flexible portion, or a combination thereof. The probe may be one piece. The probe may rotate longitudinally, axially, or both. Preferably, the probe is a single tube that oscillates longitudinally to cause destruction of a bodily calculus. Preferably, the shielding insert remains stationary during use with respect to the handpiece. The position of the probe may be monitored with sensors to determine if the tip is in contact with tissue, contact with a stone, the type of stone, if a user is applying force in excess of a predetermined threshold, or physical characteristics of the stone. Sensors may be provided at the probe tip, in the handpiece, or both.

The handpiece or handle may be any part of the device that is gripped by the user during use. The handpiece may be a central part of the device that assists in connecting or connects all of the pieces together so that the device functions as a surgical instrument. The handpiece may be a reusable part, a disposable part, or a combination thereof. Preferably, the handpiece is a reusable part that may be subjected to a sterilization process. Preferably, the handpiece may be free of components that may degrade through multiple sterilization cycles (i.e. repeated heating and cooling). More preferably, the handpiece may be free of sealing components that may degrade through multiple sterilizations. The components of the handpiece may withstand about 500 or more, preferably about 1000 or more, and more preferably about 1500 or more sterilization cycles. The handpiece may include a distal region, a central region, and a proximal region.

The distal region may be the part of the handpiece proximal to the interchangeable probe. The distal region may be in the shape of a horn. The distal region may include one or more attachment ports. Preferably, the distal region includes a probe attachment port. The probe attachment port may be any shape or size so that the probe attachment port accommodates the interchangeable probe. The probe attachment port may partially surround a portion of the interchangeable probe so that the probe is held securely in place by the probe attachment port. For example, the probe attachment port may be a "U" or "C" shape such that the interchangeable probe is securely held by the probe attachment port and the interchangeable probe is substantially restricted so that the interchangeable probe is substantially free of movement. It is contemplated that the probe being substantially restricted or substantially free of movement refers to the probe being free to move longitudinally when being driven by the driver resource but may be limited in axial movement at the point of attachment in the probe attachment port such that the oscillations produced by the driver resource may not be dampened or minimized at the point of connection to the probe attachment port. The probe attachment port may include a collet, a nut, a gripping ferrule, a ferrule, or any combination thereof in the distal region of the handpiece. The probe attachment port may be secured using a friction fit, a screw connection, or any combination thereof. The probe attachment port may be any shape that is complementary to the shape of the interchangeable probe. The probe attachment port may be a circle, square, diamond, a "D" shape, an ellipse, or combination thereof so that the interchangeable probe is properly installed in the probe attachment port and the interchangeable probe is securely connected to the handpiece. The probe attachment portion may include one or more probe locking ports.

The probe locking ports may be located anywhere in the distal region of the handpiece. Preferably, the probe locking ports may be an aperture, a through hole, a dimple, or a combination thereof in the handpiece for securing the probe in the handpiece.

The center region may be any part of the handpiece that is gripped during a procedure. The center region may be the largest portion of the handpiece. The center region may be free of any ports where other devices are inserted.

The proximal region may include a power port to supply energy to the driver resource which drives the probe. The proximal region may include one or more drain ports or fluid supply ports. The drain ports or fluid supply ports may be any feature in the handpiece that allows fluids to exit the handpiece. Preferably, the drain port allows cooling fluids to exit the handpiece after the handpiece is removed from a cooling fluid. Drain ports may be located on each side of the handpiece.

The handpiece may be provided with one or more seals, at a distal end, a proximal end, or both. The one or more seals may be located at any connection point so that fluid leakage is prevented, loss of suction is prevented, bodily waste is prevented from entering the internal lumen of the handpiece, appropriate spacing is provided to facilitate movement, or a combination thereof. The one or more seals may be located between the shielding insert and the probe, between the shielding insert and the handpiece, between the removable passageway and the shielding insert, between the probe and the internal lumen of the handpiece, or a combination thereof. The one or more seals may be o-ring seals, washers, or the like. The one or more seals may be made of any material that assists in preventing fluid leakage, is resistant to heat, is resistant to breaking down when in contact with bodily fluids, prevents loss of suction, or a combination thereof. The seals may be made of ethylene vinyl acetate (EVA), polyethylene vinyl acetate (PEVA), polyvinyl acetate (PVA), polyvinyl butyral (PVB), plastic, a polyvinyl chloride (PVC), a polytetrafluoroethylene (PTFE), a polyester, a polyvinyl fluoride (PVF), a polycarbonate, acetal, or a combination thereof. Preferably the seals may be made of silicone.

The driver resource may be any driver resource capable of producing longitudinal waves or axial rotation, or both to create an oscillatory stone destructive action at the probe distal tip. The driver resource may be any driver resource that rotates clockwise, rotates counterclockwise, expands, contracts, or a combination thereof. The driver resource may be any driver resource that may be heated in an autoclave and sanitized. The driver resource may be any driver resource that may be rapidly heated and/or cooled without performance being affected. The driver resource may be any driver resource that may be heated and cooled with driver resource parts not prematurely wearing, breaking, misaligning, or a combination thereof. The driver resource may be an enclosed driver resource so that the driver resource may be placed in a cooling fluid. For example, the driver resource may be placed in water and the water may not penetrate the outer surface of the driver resource damaging the internal components. The driver resource may be substantially sealed within the handpiece so that the driver resource power source extends out of the handpiece. By way of example, the driver resource may be a piezoelectric driver, a linear motor, a brushless DC motor, a magnetic driver, an electromagnetic driver, or a combination thereof.

A driver resource power transfer device may be provided which transfers energy from a power source to the driver resource. The driver resource power transfer device may be any power transfer device that may transfer power from the driver resource to another component so that the other component oscillates or rotates. The driver resource power transfer device may be any power transfer device that directly couples to another power transfer device so that the power transfer device is rotated. The driver resource power transfer device may directly connect to another component so that the other component is directly driven by the driver resource power transfer device. The driver resource power transfer device may transfer power to a second power transfer device that drives a component. The driver resource power transfer device may be a belt and pulley, a cog, a gear, a sprocket, a toothed wheel, a mechanism to transfer power by impact, or a combination thereof. The driver resource power transfer device may be any power transfer device that may be heated or cooled. The driver resource power transfer device may be any power transfer device that may substantially maintain its shape, form, structural attributes, tolerances, or a combination thereof when rapidly heated and cooled. The driver resource power transfer device may be made of a natural material, a synthetic material, a metal, a plastic, a polymer, or a combination thereof. Preferably the driver resource power transfer device is made of metal. The driver resource power transfer device may be located proximate to a power attachment port.

The power attachment port may be located so that a user may ergonomically grip the lithotripter so that hand strain is minimized. The power attachment port may include an attachment and/or detachment feature so that the power attachment may be connected and disconnected from the handpiece so that the handpiece may be sanitized after use. The power attachment port may be angled so that the power attachment port rests on a user's hand during use, the handpiece curves to the shape of a user's hand, the power attachment forms an angle so that the power attachment port is aligned with a user's hand and/or arm so that the weight of the power attachment is not supported solely by the user's grip.

In one embodiment, a heat exchanger may be attached to the lithotripsy device of the present invention during a sterilization procedure in order to facilitate more rapid heat transfer to the internal lumen of the handpiece. A heat exchanger is a piece of equipment built for efficient heat transfer from one medium to another. The heat exchanger may be made of copper, aluminum, carbon steel, stainless steel, nickel alloys, titanium, or a combination thereof. The heat exchanger may be externally affixed to the lithotripter, internally affixed to the lithotripter, or both. Fins may protrude radially outward from a central portion of the heat exchanger in a single plane or multiple planes to pull heat into the central lumen of the lithotripter. It is contemplated that the heat exchanger may operate optimally in temperature ranges including 100° C.-140° C., pressure ranges including 15 psi-30 psi, with pressure drops across the exchanger such as 0.5-2 psi, or with sterilization techniques that use different product mixes (i.e. liquid/liquid, particulates or high-solids liquid), for example. Preferably, the heat exchanger may be free of components that may degrade through multiple sterilization cycles (i.e. repeated heating and cooling). More preferably, the heat exchanger may be free of sealing components that may degrade through multiple sterilizations. The components of the heat exchanger may withstand about 500 or more, preferably about 1000 or more, and more preferably about 1500 or more sterilization cycles.

It is contemplated that different output accessories can be used with the device of the present invention. In one embodiment, a lithotripsy probe may be used in combination with a stone retrieval device (i.e. stone basket or stone grasper). Another embodiment might include a laser fiber used in combination with a stone retrieval device. Various other alternatives and configurations are possible to remove a calculus of interest, as discussed for example in US Patent Publication 20140121458 and are herein incorporated by reference.

It is contemplated that the device of the present invention is able to support a four minute flash cycle validation. A flash cycle may refer to heating an instrument with steam at 132 degrees Celsius for 3-4 minutes at 27-28 lbs. of pressure in a gravity displacement sterilizer. The time required for flash sterilization depends on the type of sterilizer and the item being sterilized. A device being able to support a 4 minute flash cycle validation involves challenging the device with microorganisms, performing a flash sterilization for two minutes, testing that the safety assurance level for a half cycle has a safety assurance level (SAL) of at least $10^{-10}$. If this SAL can be verified, then it may be inferred that a SAL of $10^{-12}$ may be achieved through a full sterilization (four minute cycle).

Turning now to the drawings to illustrate examples of embodiments of the present teachings, FIG. 1 details an example embodiment of a lithotripter of the present invention. Lithotripter 10 is provided with a lithotripsy probe 20 which extends through handle 28 from a handle proximal end 30 to a handle distal end 29 and, as illustrated, is secured with O-rings 25 at handle proximal end 30. Driver resource 32 is illustrated as a piezoelectric stack and provides energy to probe 20 to produce oscillatory stone destructive motion at probe distal end 22. Horn 31 extends from handle distal end 29. Probe attachment port 34 is provided at the distal end of horn 31 for securing probe 20 within handle 28. Probe distal end 22 extends beyond the distal most end of handpiece 28 and may make contact with a kidney stone during active use. Probe proximal end 23, in this embodiment, terminates proximate to the proximal end 30 of handpiece 28. Suction connector 27 is provided at the handle proximal end 30 and enables connection of a fluid source, suction source, or both. Lithotripsy probe 20 has an internal lumen 24 through which an accessory instrument, suction, or fluid may pass. In some embodiments, a removable passageway at location 33 may be provided surrounding probe 20. If probe 20 is removed after use and prior to a sterilization procedure, removable passageway at location 33 may provide extra protection against bodily waste coming into contact with the internal lumen of handle 20. A plug may optionally be provided in one end of the probe or the removable passageway prior to removal from handle 20 to further limit any bodily debris from entering the internal lumen of the device handle prior to sterilization.

Figure 2:
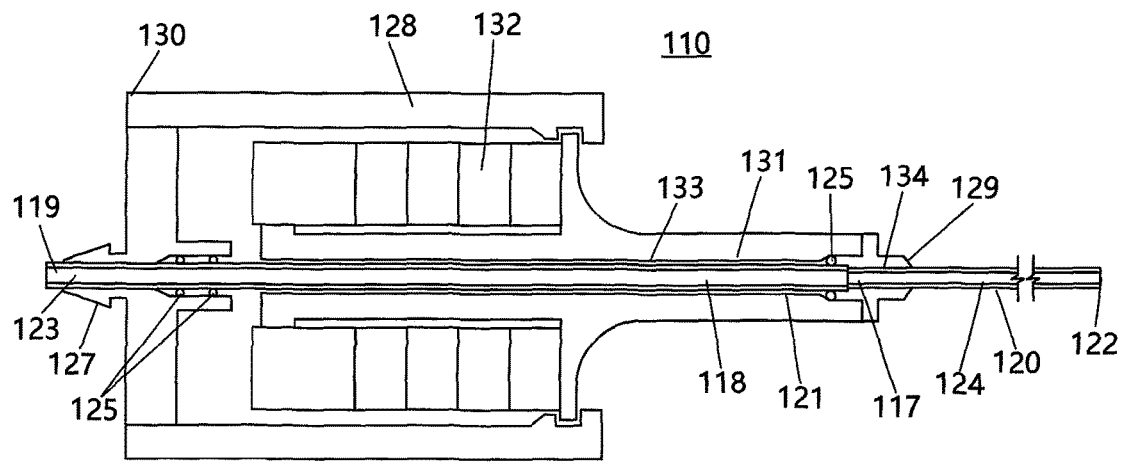
FIG. 2 is a cross-sectional view of an alternative embodiment of a lithotripter in accordance with the teachings of the present invention.

FIG. 2 illustrates another example embodiment of a lithotripter of the present invention. Lithotripter 110 is provided with a lithotripsy probe 120 which may extend through a portion of handle 128 or may terminate at a distal end of handle 128. Shielding insert 121 includes shielding insert proximal end 119 and shielding insert distal end 117 and may extend from a handle proximal end 130 to a handle distal end 129 and, as illustrated, is secured with O-rings 125 at handle proximal end 130 and handle distal end 129. One or more distal end seals, one or more proximal end seals, or a combination thereof may be provided at junction points of shielding insert 121, lithotripsy probe 120, or handle 128. Driver resource 132 is illustrated as a piezoelectric stack and provides energy to probe 120 to produce oscillatory stone destructive motion at probe distal end 122. Horn 131 extends within handle distal end 129. Probe attachment port 134 is provided at the distal end of horn 131 for securing probe 120 within handle 128. Probe distal end 122 extends beyond the distal most end of handpiece 128 and may make contact with a kidney stone during active use. Probe proximal end 123, in this embodiment, terminates within shielding insert 121. Suction connector 127 is provided at the handle proximal end 130 and enables connection of a fluid source, suction source, or both. Lithotripsy probe 120 has an internal lumen 124 through which an accessory instrument, suction, or fluid may pass. In some embodiments, removable passageway 133 may be provided surrounding probe 120. If probe 120 is removed after use and prior to a sterilization procedure, removable passageway 133 may provide extra protection against bodily waste coming into contact with the internal lumen of handle 120. A plug may optionally be provided in one end of the probe 120 or the removable passageway 133 prior to removal from handle 128 to further limit any bodily debris from entering the internal lumen of the device handle prior to sterilization.

Figure 3:
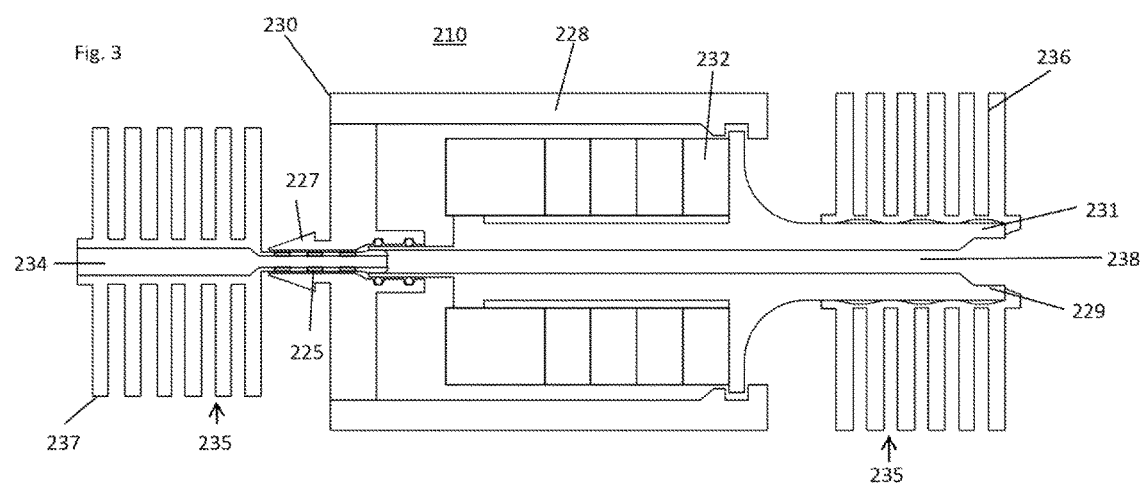
FIG. 3 is a cross-sectional view of an alternative embodiment of a lithotripter in accordance with the teachings of the present invention.

FIG. 3 illustrates another example embodiment of a lithotripter of the present invention prepared for a sterilization procedure. A lithotripsy probe, shielding insert, removable passageway, or a combination thereof, may have been removed from central lumen 238 of lithotripter 210. Alternatively, heat exchangers may be added to the device without removing any internal lumens. Driver resource 232 is illustrated as a piezoelectric stack maintains enclosed within handle 228 during a sterilization procedure. Horn 231 extends within handle distal end 229. Heat exchanger 235 may be attached to the lithotripter prior to performing a sterilization procedure and may consist of a distinct heat exchanger proximal portion 237 and heat exchanger distal portion 236. Suction connector 227 is provided at the handle proximal end 230 and enables connection of a heat exchanger 237 at handle proximal end 230. Seals 225 may be provided to help secure heat exchanger into suction connector 227. An additional heat exchanger 236 is provided at handle distal end 229 and surrounds the outside of horn 231.

Figure 4:
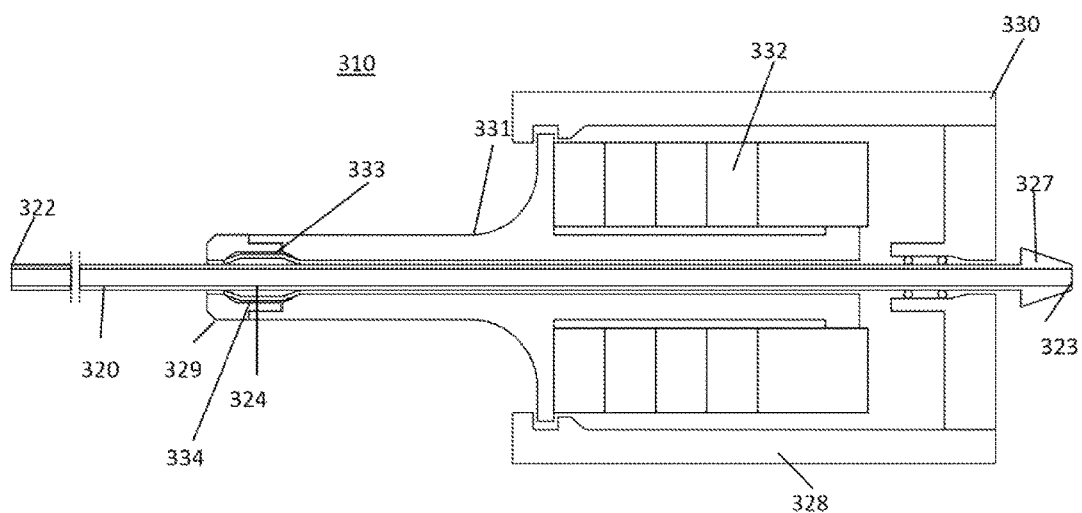
FIG. 4 is a cross-sectional view of an alternative embodiment of a lithotripter in accordance with the teachings of the present invention.

FIG. 4 illustrates another example embodiment of a lithotripter of the present invention. Lithotripter 310 is provided with a lithotripsy probe 320 which extends through a portion of handle 328 from a handle proximal end 330 to a handle distal end 329. Driver resource 332 is illustrated as a piezoelectric stack and provides energy to probe 320 to produce oscillatory stone destructive motion at probe distal end 322. Horn 331 extends within handle distal end 329. The probe attachment port is illustrated as split collet 333 provided with a screw connection for securing probe 320 into handle 328. Probe distal end 322 extends beyond the distal most end of handpiece 328 and may make contact with a kidney stone during active use. Probe proximal end 323, in this embodiment, terminates at the proximal end of handle 328. Suction connector 327 is provided at the handle proximal end 330 and enables connection of a fluid source, suction source, or both. Lithotripsy probe 320 has an internal lumen 324 through which an accessory instrument, suction, or fluid may pass. In some embodiments, removable passageway 333 (not shown) may be provided surrounding probe 320. If probe 320 is removed after use and prior to a sterilization procedure, removable passageway 333 may provide extra protection against bodily waste coming into contact with the internal lumen of handle 328. A plug may optionally be provided in one end of the probe 320 or the removable passageway 333 prior to removal from handle 328 to further limit any bodily debris from entering the internal lumen of the device handle prior to sterilization.

Figure 5:
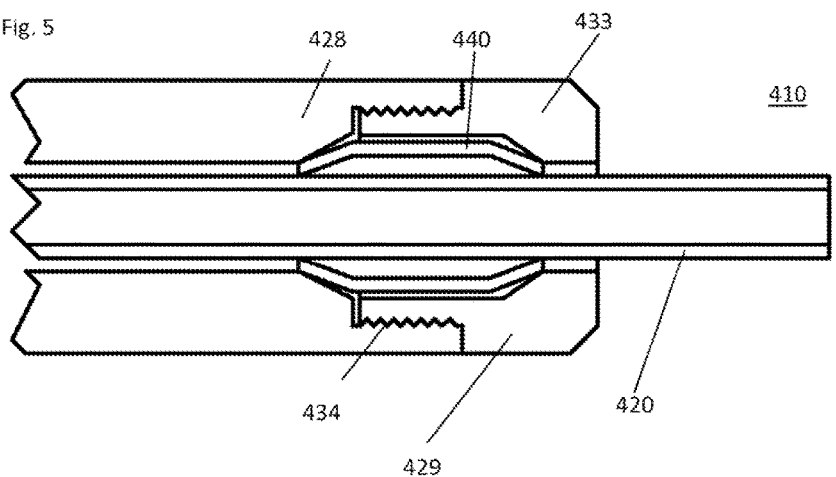
FIG. 5 is an exploded cross sectional view of one embodiment of a distal end of a lithotripter handpiece in accordance with the teachings of the present invention.

FIG. 5 illustrates another example embodiment of a probe attachment port of a lithotripter of the present invention. Lithotripter 410 is provided with a lithotripsy probe 420 which extends through a portion of distal portion 429 of handle 428. The probe attachment port is illustrated as collet 433 provided with a screw connection 434 for securing probe 420 into handle 428. Ferrule 440 is provided to create a friction fit seal securing probe 420 in place and creating a seal to prevent liquid or bodily waste from entering a central lumen of lithotripter 410.

It is contemplated embodiments or examples described above may not be mutually exclusive and may be used in combination with each other.

Unless stated otherwise, dimensions and geometries of various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

Preferred embodiments of the present invention have been disclosed. A person of ordinary skill in the art would realize, however, that certain modifications would come with the teachings of the invention. Therefore, the following claims should be studied to determine the true scope and content of the invention.

Any numerical values recited in the above application include all values from the lower value to the upper value in increments of one unit provided that there is a separation of at least two units between any lower value and any higher value. As an example if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01, or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" and "approximately" in connection with a range applies to both ends of the range. Thus, "about 20 to about 30" is intended to cover "about 20 to about 30." Inclusive of at least the specified endpoints.

The disclosures of all articles and references, including patent applications and publications, are incorporated by reference for all purposes.

The term "consisting essentially of to describe a combination shall include the elements, ingredients, components or steps identified, and such other elements, ingredients, components or steps that do not materially affect the basic and novel characteristics of the combination.

The use of the terms "comprising" or "including" describing combinations of elements, ingredients, components or steps herein also contemplates embodiments that consist essentially of the elements, ingredients, components or steps.

Plural elements, ingredients, components or steps can be provided by a single integrated element, ingredient, component or step might be divided into separate plural elements, ingredients, components or steps. The disclosure of "a" or "one" to describe an element, ingredient, component or step is not intended to foreclose additional elements, ingredients, components, or steps.

LIST OF ELEMENTS

10 Lithotripter
20 Lithotripsy shaft
22 Lithotripsy shaft distal end
23 Lithotripsy shaft proximal end
24 Lithotripsy shaft lumen
25 O ring
27 Suction connector
28 Handle
29 Handle distal end
30 Handle proximal end
31 Horn of driver resource
32 Driver Resource
33 Removable passageway
34 Shaft attachment port (at distal end of horn)
110 Lithotripter
117 Shielding insert distal end
118 Shielding insert lumen
119 Shielding insert proximal end
120 Lithotripsy shaft
121 Shielding insert
122 Lithotripsy shaft distal end
124 Lithotripsy shaft lumen
125 O ring
127 suction connector
128 Handle
129 Handle distal end
130 Handle proximal end
131 ultrasonic horn
132 Driver resource
133 Removable passageway
134 Connector (at distal end of horn)
210 Lithotripter
225 O ring
227 Suction connector
228 Handle
229 Handle distal end
230 Handle proximal end
231 Driver resource horn
232 Driver resource
234 Heat exchanger lumen
235 Heat exchanger
236 Heat exchanger distal portion
237 Heat exchanger proximal portion
238 Lumen
239 Lithotripter distal end
310 Lithotripter
320 Lithotripsy Shaft
322 Lithotripsy shaft distal end
323 Lithotripsy shaft proximal end
324 internal lumen of shaft
327 Suction connector
328 Handle
329 Handle distal end
330 Handle proximal end
331 Horn of driver resource
332 Driver Resource
333 Split Collet
334 Screw connection
410 Lithotripter
420 Lithotripsy Shaft
428 Handle
433 Collet
434 Screw connection
440 Ferrule

The invention claimed is:

1. An apparatus, comprising:
a lithotripter, comprising:
a handle, the handle having a handle distal end and a handle proximal end;
a driver resource contained within the handle, the driver resource having a driver resource distal end and a driver resource proximal end;
a probe housed within the handle, the probe having a probe distal end and a probe proximal end, the probe distal end terminating at the distal end of the apparatus at a point distal from the handle distal end, the probe proximal end terminating proximal to the driver resource proximal end;
a removable passageway extending through the handle and at least partially containing the probe, the removable passageway having a removable passageway proximal end and a removable passageway distal end; and
a shielding insert surrounding at least a portion of the probe, the shielding insert having a shielding insert proximal end and a shielding insert distal end, the shielding insert proximal end terminating proximal to the proximal end of the driver resource, the shielding insert being contained in the removable passageway,
wherein the probe proximal end is contained within the handle,
wherein the driver resource causes the probe to move in a direction parallel with a longitudinal axis of the probe,
wherein the handle further comprises one or more distal end seals, one or more proximal end seals, or a combination thereof positioned adjacent to the shielding insert and between the shielding insert and the handle to provide a fluid tight sealing directly adjacent to the shielding insert.

2. The apparatus of claim 1, wherein the one or more distal end seals, the one or more proximal end seals, or both are o-rings.

3. The apparatus of claim 1, wherein the removable passageway proximal end terminates proximal to the proximal end of the driver resource.

4. The apparatus of claim 1, wherein the one or more distal end seals are located distal to the driver resource distal end and the one or more proximal end seals are located proximal to the driver resource proximal end.

* * * * *